United States Patent [19]

Sugano et al.

[11] Patent Number: 5,326,859
[45] Date of Patent: Jul. 5, 1994

[54] DNA AND RECOMBINANT PLASMID

[75] Inventors: Haruo Sugano, Tokyo; Masami Muramatsu, Tokorozawa; Tadatsugu Taniguchi, Tokyo, all of Japan

[73] Assignee: Juridical Foundation, Japanese Foundation for Cancer Research, Tokyo, Japan

[21] Appl. No.: 201,359

[22] Filed: Oct. 27, 1980

[51] Int. Cl.$^5$ ............... C12N 15/22; C12N 15/00
[52] U.S. Cl. .................. 536/23.52; 435/69.51; 435/172.3; 435/320.1
[58] Field of Search ......... 536/27, 23.52; 435/172, 435/317, 91, 69.51, 243, 252.33, 172.3, 320.1, 91.1

[56] References Cited

PUBLICATIONS

Taniguchi et al, Gene 10 pp. 11-15 (1980).
Houghton, Nature vol. 285 p. 536 Jun. 19, 1980.
Derynch et al, Nature vol. 285 pp. 542-549 Jun. 19, 1980.
Research Disclosure #18309 Jul. 1979.
Taniguchi, et al., Proc. Japan Acad., 55(B), Nov. 12, 1979 published Dec. 8, 1979.
Taniguchi, et al., Proc. Natl. Acad. Sci., U.S.A., vol. 77(7), Jul. 1980.

Primary Examiner—James Martinell
Attorney, Agent, or Firm—White & Case

[57] ABSTRACT

Disclosed is a recombinant plasmid having a gene which encompasses at least the entire coding region of human fibroblast interferon messenger RNA and a method for preparing such plasmid.

9 Claims, 1 Drawing Sheet

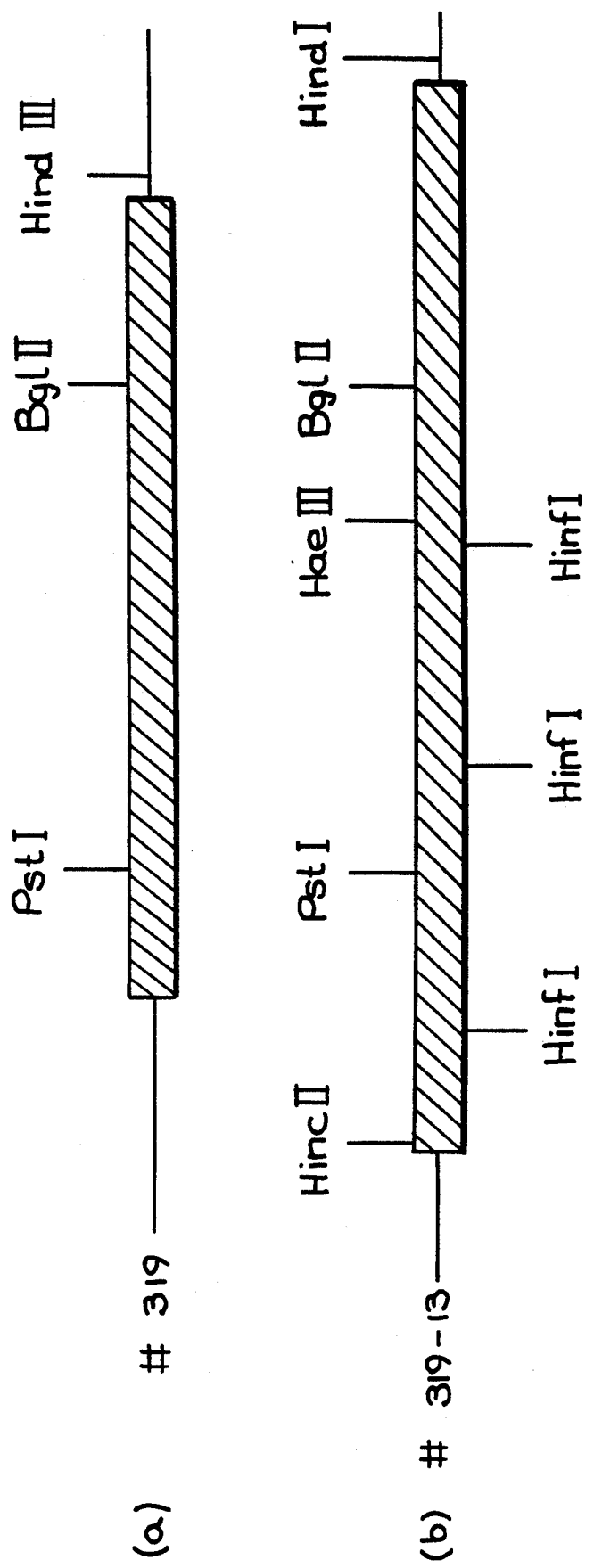

DNA AND RECOMBINANT PLASMID

BACKGROUND OF THE INVENTION

The present invention relates to a DNA which codes for a polypeptide with interferon activity and a recombinant plasmid containing the DNA. The present invention also pertains to a microorganism containing the recombinant plasmid.

Interferon is a glycoprotein (molecular weight approx. 20,000) with antiviral activity, discovered by Isaacs and Lindenmann in 1957. Subsequent studies have indicated antitumor activity of the substance in addition to antiviral activity and hence a wide clinical application of this substance is expected. For instance, it has been reported that interferon may be effectively administered to various vital diseases, osteosarcoma and mammary carcinoma.

However, because of its high species-specificity, only the interferon derived from human cells can be used for human application. At present, the interferon which is being used for administration has a relative activity of about $10^6$ (International units) per 1 mg, which corresponds to a purity of about 0.1–0.01%.

Moreover, the use of the interferon is quite limited because of difficulties in mass-production. At present even for the interferon requirement for clinical tests ($10^{13}$ units per year), the supply is only about 1%. For these reasons, development of technology to produce human interferon in high purity, with ease and in large quantities is in demand.

To this end, a novel technique has been developed for producing interferon with ease and in a large quantity by inserting a human interferon gene into a plasmid DNA (for instance plasmid DNA derived from *Escherichia coli*) with recombinant DNA (deoxyribonucleic acid) technology.

SUMMARY OF THE INVENTION

In accordance with the present invention, a DNA which codes for a polypeptide with interferon activity is prepared using the human interferon messenger RNA as a template and a novel recombinant plasmid containing the DNA is prepared. In addition, the recombinant plasmid may be inserted into a host microorganism.

The DNA which codes for a polypeptide with interferon activity and the recombinant plasmid containing the DNA have been obtained for the first time by the present inventors. The DNA and the recombinant plasmid may be used, inter alia, for amplification of human interferon in bacteria such as *Escherichia coli*. Such bacteria are then useful for the production of human interferon in large quantities at low cost.

The DNA and the recombinant plasmid of the present invention are prepared by the following general procedure.

First, cytoplasmic RNA is extracted from (1) human fibroblast, MG63 cells or others induced by poly(I): poly(C) which is a double stranded RNA composed of polyinosinic acid and polycytidylic acid or other inducers, (2) human leucocyte, lymphoblastic cells, NAMALWA cells or others induced by Sendai virus or other inducers, or (3) lymphocytes induced by various mitogens or other inducers. From this RNA, the human interferon messenger RNA (hereinafter messenger RNA is referred to as mRNA) containing poly A (polyadenylic acid) is isolated. A double stranded DNA is synthesized, for example, by reverse transcriptase, with the mRNA preparation having high interferon mRNA activity, as a template. A recombinant is obtained by inserting the synthesized DNA into a vector DNA such as *Escherichia coli* plasmid DNA by the technique of in vitro DNA recombination. The recombinant is labelled with a radio isotope for use as a probe. Recombinant plasmids having an inserted portion which is complementary to the human interferon mRNA are selected. The DNA which codes for a polypeptide with interferon activity is recovered from the recombinant plasmid and the base sequence of the DNA is determined.

BRIEF DESCRIPTION OF THE DRAWINGS

FIG. 1 illustrates restriction endonuclease maps of:

(a) a gene which shows complementarity to the human fibroblast interferon mRNA in the recombinant #319 used to make a novel recombinant plasmid #319-13; and (b) a gene which shows complementarity to the human fibroblast interferon mRNA in the novel recombinant plasmid #319-13.

DETAILED DESCRIPTION OF THE PRESENT INVENTION

The present invention relates to a DNA which codes for a polypeptide with interferon activity, a recombinant plasmid containing the DNA and a microorganism containing the recombinant plasmid.

The DNA of the present invention may be a cloned DNA showing complementarity to the human interferon mRNA, a cloned DNA which codes for a polypeptide with interferon activity or a cloned DNA which codes for human interferon polypeptide. Especially a DNA which encompasses the entire coding region of the human fibroblast interferon (i.e. human B, interferon) mRNA is a preferred example of the DNA of the present invention.

The recombinant plasmid of the present invention is a recombinant plasmid wherein the DNA mentioned above is inserted in a vector DNA such as pBR322, pCR1, or pMB9.

The recombinant plasmids named #319 and #319-13 are preferred examples of a recombinant plasmid according to the invention.

The DNA and the recombinant plasmid are inserted in a host microorganism and the transformant can be used to produce a substance having interferon activity.

As the host microorganism, *Escherichia coli* χ1776 is preferably used.

An example of the processes of producing the DNA, the recombinant plasmid and the transformant of the present invention is as follows.

First, human fibroblasts may be obtained from fetus-derived foreskin, or the like. A small amount of interferon is then added to a culture fluid of human fibroblasts to prime the interferon synthesis by human fibroblasts, to which poly (I): poly (C) is added to induce the synthesis of interferon mRNA. Cycloheximide is added simultaneously to increase the level of interferon mRNA. At an appropriate time (about 4 hours) after the human fibroblasts are superinduced in the above manner, cells are collected and destroyed and the nuclei are removed. Cytoplasmic total RNA is extracted with phenol, or the like. The RNA can also be extracted by destroying the whole cells, extracting both DNA and RNA with, for example, phenol, and degrading and removing the DNA with DNAase.

Further, interferon mRNA can also be extracted from MG63 cells induced by poly (I): poly (C) or other inducers, human leucocyte or lymphoblastic cells induced by Sendai virus or other inducers, and lymphocytes induced by various mitogens or other inducers.

The thus extracted RNA is dissolved in a salt solution of NaCl or KCl at a high concentration such as 0.5M and put on a column of oligo (dT) cellulose to adsorb mRNA having poly (A) on the column. Elution is carried out with water, a salt solution at a low concentration such as 10 mM Tris-HCl buffer, or the like to isolate mRNA having poly (A).

The isolated mRNA is fractionated by sucrose density gradient centrifugation. Interferon mRNA activity in each fraction is checked by determining interferon activity (antiviral activity) of the protein which is synthesized in oocytes of African claw toad (*Xenopus laevis*) after microinjecting a part of the mRNA in each fraction. The determination of interferon activity is carried out according to the method described in Japan J. Microbiol. 18, 449–456, (1974).

Then, a DNA showing complementarity to the mRNA is synthesized in vitro by a reverse transcriptase, which is obtained from arian myeloblastosis virus, using, as the template, a mRNA having the highest interferon mRNA activity.

The synthesis is carried out as follows.

A mRNA is reacted at an appropriate temperature (e.g. 37° C.) for an appropriate period (e.g. 60 min.) with oligo (dT), $MgCl_2$ (e.g. 5 mM), NaCl (e.g. 30 nM), mercaptoethanol (e.g. 5 mM) and Tris-HCl buffer (e.g. pH 8.0, 40 mM) using a reverse transcriptase together with deoxyadenosine triphosphate (dATP), deoxythymidine triphosphate (dTTP), deoxyguanosine triphosphate (dGTP) and deoxycytidine triphosphate (dCTP) (e.g. 0.5 mM each) as substrates.

The thus obtained reaction product is subjected to deproteinization with, for example, phenol, and the template RNA is removed by alkali or ribonuclease treatment. A double stranded DNA is synthesized by a reverse transcriptase in a similar way as the synthesis of the DNA showing complementarity to mRNA described above except that mRNA is replaced by DNA and oligo (dT) is omitted.

By using *Escherichia coli* DNA polymerase I which can be obtained from *Escherichia coli* MRE 600, or the like, instead of reverse transcriptase, the same double stranded DNA can be synthesized.

After the double stranded DNA which is synthesized by the above described procedure is treated with Nuclease $S_1$ which can be obtained from *Aspergillus oryzae* in the presence of $ZnCl_2$ (e.g. 1 mM), sodium acetate buffer (e.g. 0.1M, pH 4.5), NaCl (e.g. 0.2M), etc., deoxyadenine chains are formed at both 3' ends of the synthesized DNA by incubating with a terminal transferase purified from calf thymus in the presence of potassium cacodylate buffer (e.g. pH 7.6, 0.14M), Tris (base) (e.g. 0.03M), dithiothreitol (e.g. 0.1 mM), $CoCl_2$ (e.g. 1 raM) and dATP (e.g. 1 mM) at an appropriate temperature (e.g. 37° C.) for an appropriate period (e.g. 20 min.)

On the other hand, a plasmid DNA which is used as a vector DNA, e.g. *Escherichia coli* plasmid pBR322 DNA [Gene vol. 2, p. 95–113 (1977)], is cleaved at one site by treating with a restriction endonuclease EcoRI, which can be obtained, for example, from *Escherichia coli* RY13, in the presence of Tris HCl buffer (e.g. pH 7.5, 10 mM), $MgCl_2$ (e.g. 6 mM), NaCl (e.g. 0.1M), mercaptoethanol (e. g. 6 mM), or the like and then treated with phage h-derived exonuclease, which can be obtained, for example, from *Escherichia coli* W3102 (λcI851) ×13), in the presence of Na-glycine buffer (e.g. pH 9.5, 0.1M), $MgCl_2$ (e.g. 5 mM), or the like. Thereafter deoxythymidine chains are formed at both 3' ends in the same way as for the above-described synthesized double stranded DNA by using dTTP instead of dATP.

Synthetic double stranded DNA and plasmid DNA which are chain-elongated at both 3' ends as described above are incubated at an appropriate temperature for an appropriate period with Tris- HCl buffer (e.g. pH 7.5, 50 mM), NaCl (e.g. 0.1M), EDTA (e.g. 5 mM), or the like and hybridized with hydrogen bonds formed by adenine and thymine. Then, a transformable *Escherichia coli* strain, e.g. *Escherichia coli* χ1776 (Molecular Cloning of Recombinant DNA, Scott, W. A. & Werner, R. edited, Academic Press p. 99–114, 1977) is transformed with the hybridized DNA by the method of Enea et al. (J. Mol. Biol. vol. 96, p. 495–509, 1975) or the like, In the novel recombinant plasmid DNA thus obtained, there exists a vector DNA gene, e.g. β-lactamase (enzyme that destroys ampicillin) gene, of *Escherichia coli* plasmid pBR322. Therefore, the transformed *Escherichia coli* shows resistance to ampicillin. The following technique is used to pick up a strain with a novel recombinant having a gene which shows complementarity to the human interferon messenger RNA among these ampicillin resistant strains.

First, [$^{32}$p] labelled DNA is synthesized with the RNA having interferon mRNA activity described above as a template and the DNA is hybridized with mRNA extracted, without induction by poly(I): poly(C) (therefore, interferon mRNA synthesis is not induced), from the human fibroblasts by incubating at a high temperature (e.g. 65° C.) in a reaction mixture containing, for example NaCl (e.g. 0.5M). Then, the hybridized DNA (Probe A) and non-hybridized DNA (Probe B) are separated by hydroxyapatite column chromatography. Next, filter-fixed DNAs of transformants are hybridized separately with Probe B or Probe A according to the technique of Grunstein-Hogness (Proc. Nat. Acad. Sci. USA, vol. 72, p. 3961–3965, 1975) and strains having a DNA hybridizable with Probe B but not or barely with Probe A are discerned by autoradiography.

Then, plasmid DNA is isolated from each of the discriminated strains and hybridized with mRNA having interferon mRNA activity by incubating at a high temperature (e.g. 53° C.) in the presence of 80% (w/v) formamide, 0.4M NaCl, etc. Since the mRNA hybridized with cDNA portion of the plasmid DNA from the above-described strain can be retained on a nitrocellulose filter, whereas unhybridized mRNA can not under certain conditions (refer to Example below and Nygaard, A. P. & Hall, B. D., Biochem. Biophys. Res. Commun. Vol. 12, p. 98–104, 1963) this mRNA can be recovered selectively from the filter at a high temperature (e.g. 60° C.) in a solution such as 90% (v/v) formamide and thereafter injected into oocytes of Xenopus laevis.

When interferon is synthesized in the oocytes, the DNA used for hybridization must contain a DNA which is complementary to interferon mRNA; and by this method, a recombinant plasmid DNA having a gene showing complementarity to the human fibroblast interferon mKNA can be isolated.

The recombinant plasmid DNA obtained above or segments cleaved with a restriction endonuclease are labelled with a radio isotope such as $^{32}P$ by Nick-translation method (Rigby, et al., J. Mol. Biol. vol. 113, p. 237-251, 1977), or the like, and used as a probe to obtain *Escherichia coli* strains containing a recombinant plasmid having the interferon mRNA sequence from the above ampicillin resistant strains in the same way as described above. Several strains thus obtained are cultured and the plasmid DNA is isolated therefrom. The plasmid DNA is cleaved with a restriction endonuclease to obtain the inserted DNA. The length of the inserted DNA is investigated to obtain a plasmid having an inserted DNA coding the entire region of the interferon protein. Primary structure of the inserted DNA of one of recombinant plasmids isolated by the above method is determined according to the Maxam-Gilbert method (Proc. Nat. Acad. Sci. U.S.A. vol. 74, p. 560-564, 1977) and is illustrated in the following Example. It has thus been shown that the recombinant plasmid of the invention contains the entire coding region of the human fibroblast interferon mRNA.

As outlined above, a DNA which codes for human fibroblast interferon polypeptide, especially a DNA which encompasses the entire coding region of the human fibroblast interferon mRNA, a recombinant plasmid containing the DNA and a microorganism containing the plasmid are prepared.

The base sequence of the DNA obtained above and the corresponding peptide sequence are illustrated in Table 5 below.

The base sequence in Table 5 is a preferred example for the expression of the DNA which codes for human interferon polypeptide. Since the amino acids in the peptide sequence in Table 5 may be coded for by a base triplet other than those in Table 5, base sequences of the DNA which codes for human interferon polypeptide other than that in Table 5 are also included in the present invention.

The determination of the base sequence of the DNA which codes for human interferon polypeptide according to the present invention has enabled the chemical synthesis of such DNA.

The present novel recombinant plasmids having a gene which encompasses at least the entire coding region of the human fibroblast interferon mRNA are very useful because they enable mass production of interferon in *Escherichia coli* or in eukaryotic cells which can be grown on a large scale.

Recombinant plasmids containing a DNA using, as a template, leucocyte mRNA or immune interferon mRNA can be prepared by the same method as mentioned above and such plasmids are also expected to be useful for the mass production of interferon.

One specific embodiment of the present invention is illustrated by the following representative example.

EXAMPLE

After priming of human fibroblasts by overnight incubation with MEM culture medium (product of Nissui Seiyaku Co., Ltd., Japan) containing human interferon which is prepared according to the method described in Proc. Nat. Acad. Sci. USA, 73, 520-523 (1976) (25 U/ml), the fibroblasts were superinduced by adding 10 $\mu$g/ml of poly(I): poly(C) (product of Galbiochem Co., USA) and 5 $\mu$g/ml of cycloheximide to the medium. The priming and superinduction are carried out according to the methods described in Brit. J. Exp. Path., 39, 452-458 (1958) and Antimicrob. Agents Chemother., 2, 476-484 (1972), respectively.

After 4 hours, $1.5 \times 10^9$ superinduced human fibroblasts were destroyed by Teflon homogenizer (sold by Takashima Shoten Co., Japan) at a temperature of 0° to 4° C. in the presence of 0.3% NP-40 (product of Daiichi Kagaku Co., Japan) and 50 $\mu$g/ml heparin in RSB buffer (10 mM Tris-HCl, pH 7.5; 10 mM NaCl; 1.5 mM $MgCl_2$). Nuclei were removed by centrifugation at 3000 rpm and 4° C. for 10 minutes and 9.6 mg of cytoplasmic RNA was obtained by extraction 3 times with phenol.

The cytoplasmic RNA was precipitated with 67% ethanol in the presence of 0.1M NaCl, dissolved in 10 ml of 1 mM EDTA solution and incubated at 65° C. for 2 minutes. Then, 2.5 ml of a salt solution at a high concentration (0.5M Tris-HCl, pH 7.5; 1M NaCl; 50 mM EDTA) was added to the above solution and the mixture was put on a column packed with 0.15 g of an oligo(dT) cellulose (product of P-L Biochemicals Co., USA) to adsorb mRNA containing poly(A). Elution was then carried out with a salt solution at a low concentration (10 mM Tris-HCl, pH 7.5) and water to isolate 250 $\mu$g of mRNA containing poly(A).

The mRNA was precipitated with 67% ethanol in the presence of 0.1M NaCl and dissolved in 0.5 ml of 1 mM EDTA solution. The solution was incubated at 65° C. for 2 minutes, subjected to centrifugation through a 5-25% sucrose-density gradient containing 50 mM Tris-HCl, pH 7.5, 0.2M NaCl and 1 mM EDTA (rotated at 35,000 rpm using the SW40 rotor of Beckmann Co., U.S.A.) at 4° C. for 16 hrs. and fractionated into 20 fractions.

The interferon mRNA activity of each of these fractions was determined as mentioned above, and the results are shown in Table 1 below.

TABLE 1

| Fraction No. | Interferon Activity |
| --- | --- |
| 9 | <50 units/ml |
| 10 | 44 |
| 11 | 550 |
| 12 | 52 |

The mRNA in Fraction No. 11 was approximately 5 $\mu$g. This mRNA and a reverse transcriptase were incubated at 37° C. for an hour in 20 $\mu$l of a reaction mixture consisting of 5 $\mu$g mRNA; 0.5 mM dATP; 0.5 mM dTTP; 0.5 mM dGTP; 0.5 mM dCTP; 1 $\mu$g oligo(dT) (product of P-L Biochemicals Co., USA); 8 units reverse transcriptase (derived from Avian myeloblastisis virus, for example, product of Life Science Inc. Florida, USA); 5 mM $MgCl_2$; 30 mM NaCl; 5 mM mercaptoethanol; and 40 mM Tris- HCl (pH 8.0) and then deproteinized with phenol. After RNA was removed by treatment with 0.3N NaOH at 37° C. for 15 hours, the synthesized single stranded DNA was incubated at 37° C. in 20 $\mu$l of a reaction mixture [the same mixture as described above except that mRNA and oligo(dT) were omitted] for one hour to synthesize 1.5 $\mu$g of a double stranded DNA.

The double stranded DNA was treated with Nuclease $S_1$ (product of Bethesda Research Laboratories Inc., USA which is referred to as BRL, hereinafter) in 50 $\mu$l of a reaction mixture (1.5 $\mu$g double stranded DNA: 1 mM $ZnCl_2$; 0.1M sodium acetate, pH 4.5; 0.2M NaCl; 0.05 unit $S_1$) at 37° C. for 30 minutes and the enzyme was removed by phenol extraction. The DNA was precipitated with ethanol and then treated with a terminal transferase in 20 μl of a reaction mixture consisting of 1.5 μg DNA; 0.14M potassium cacodylate, pH 7.6; 0.03M Tris (base); 0.1 mM dithiothreitol; 1 mM COCl₂; 1 mM dATP; and 1 unit terminal transferase (product of BRL) at 37° C. for 20 minutes to obtain about 1.5 μg of a product wherein 100 deoxyadenosine chains were formed at both 3' ends of the double-stranded DNA.

On the other hand, 10 μg of *Escherichia coli* plasmid pBR322 DNA (product of BRL) was treated at 37° C. for 2 hours with a restriction endonuclease EcoRI in 100 μl of a reaction mixture consisting of 10 mM Tris-HCl, pH 7.5; 6 mM MgCl₂; 0.1M NaCl; 6 mM mercaptoethanol; and 10 units EcoRI (product of BRL) leading to the cleavage at the only one cutting site in pBR322 DNA. The cut plasmid DNA was treated with an exonuclease derived from phage λ in 200 μl of a reaction mixture consisting of 10 μg DNA; 0.1M Naglycine, pH 9.5; 5 mM MgCl₂; 50 μg/ml albumin (product of Merck & Co., USA); and 17.5 units λ exonuclease (product of Miles Laboratories Inc., USA) at 0° C. for 90 minutes and the enzyme was removed by phenol extraction. The DNA was treated with a terminal transferase in 50 μl of a reaction mixture [10 μg DNA; 0.14M potassium cacodylate, pH 7.6; 0.03M Tris (base); 0.1 mM dithiothreitol; 1 mM COCl₂; 1 mM dTTP; 2 units terminal transferase] at 37° C. for 20 minutes to obtain about 0.5 μg of a product wherein 100 deoxythymidine chains were formed at both 3' ends of plasmid pBR322 DNA described above.

Then, 0.02 μg of the synthesized double stranded DNA obtained above, and 0.1 μg of the plasmid pBR322 DNA were incubated for hybridization in a solution containing 0.1M NaCl, 50 mM Tris- HCl (pH 7.5) and 5 mM EDTA at 65° C. for 2 minutes, at 45° C. for one hour, at 37° C. for one hour and at room temperature for one hour. Then, *Escherichia coli* χ1776 was transformed with the hybridized recombinant following the method of Enea et al.

About 4,000 ampicillin-resistant strains were isolated by this method. 3,600 resistant strains were chosen, and the DNA of each strain was fixed on nitrocellulose filters in duplicate (Grunstein-Hogness Method).

On the other hand, [³²p] labelled single stranded DNA was synthesized (about 0.44 μg, specific radioactivity approx. 6×10⁸ c.p.m./μg) by a reverse transcriptase in the same way as that for single stranded DNA mentioned above (dCTP was labelled with ³²p) using the interferon mRNA fraction (about 10 μg) which had been extracted and partially purified as described above, as a template. The DNA was hybridized in 50 μl of a reaction mixture (25 μg mRNA; 0.45 μg single stranded DNA labelled with ³²p; 0.5M NaCl; 25 mM Pipes buffer, pH 6.5) at 65° C. for 40 hours with 25 μg of mRNA extracted from human fibroblasts which had not been induced by poly(I): poly(C). The latter mRNA was prepared by the same method used to extract poly(I): poly(C)-induced mRNA. The reaction mixture was put on a column packed with 0.2 g of a hydroxyapatite, and elution was first carried out with 5 ml of 0.14M phosphate buffer (pH 6.5) to elute the single stranded DNA, and then with 5 ml of 0.4M phosphate buffer to elute the DNA hybridized with RNA. As the result, the DNA (about 90% of the whole) (Probe A) which hybridized with the mRNA mentioned above, and the DNA (about 10% of the whole) (Probe B) which did not hybridize were isolated.

Each probe was then hybridized separately with the above DNA fixed on the nitrocellulose filters according to the Grunstein-Hogness method. Four strains were identified which reacted mainly to Probe B but little to Probe A by autoradiography.

Table 2 shows the extent of reaction of the DNAs from the four strains to each probe as revealed by autoradiogram.

TABLE 2

| Ampicillin-resistant strains | Extent of Reaction of Probe with DNA in the strains | |
|---|---|---|
| | Probe A | Probe B |
| #319 | + + | + + + + |
| #644 | + | + + + |
| #746 | − | + + |
| #3578 | + | + + + + |

Plasmid DNA was isolated from cells of the four strains by the method of Currier and Nester (Analyt. Biochem. vol. 76, p. 431–441, 1976). Then, these DNAs were hybridized with the interferon mRNA as follows.

First, 5 μg of plasmid DNA was linearized by incubating with restriction endonuclease Hind III which can be obtained from Haemophilus influenzae Rd in 50 μl of a reaction mixture consisting of 10 mM Tris-HCl, pH 7.5; 6 mM MgCl₂; 50 mM NaCl; 6 mM mercaptoethanol; and 5 units Hind III (product of BRL) at 37° C. for 2 hours. After deproteinization by phenol extraction, the DNA was precipitated with ethanol and dissolved in 20 μl of 80% (w/v) formamide. The solution was denatured at 85° C. for 10 minutes and was then incubated in a solution consisting of 2.5 μg mRNA, 20 μl 80% (w/v) formamide, 20 mM Pipes buffer (pH 6.5), 0.4M NaCl and 5 mM EDTA, at 53° C. Four hours later the mixture was mixed with 0.4 ml of 3×SSC (1×SSC corresponds to 0.15M NaCl, 0.015M sodium citrate) at 0° C., and was filtered through a nitrocellulose filter (diameter:1 cm, pore size: 0.45 μm) at a rate of about 0.5 ml per minute. After washing the filter with about 1.5 ml of 2×SSC, the filter was immersed in a solution consisting of 0.6 ml of 90% (v/v) formamide, 20 mM Pipes buffer, 0.1% SDS (sodium dodecylsulfate) and 5 mM EDTA. Incubation of the filter at 60° C. for 2 minutes and the removal of the solution were repeated 3 times and the NA eluted from the nitrocellulose filter into the solution (1.8 ml) was precipitated with ethanol in the presence of 0.1M NaCl. The mRNA containing poly(A) was isolated from the RNA by using oligo(dT) cellulose column chromatography, dissolved in a mixture of 3 μl of 10 mM Tris- HCl (pH 7.5) and 88 mM NaCl and injected into the oocytes of *Xenopus laevis*. After 15 hours, the interferon synthesized in the oocytes was determined (antiviral activity).

Table 3 shows the interferon mRNA activity of the mRNA which has hybridized with the DNA derived from the four bacterial strains mentioned above.

TABLE 3

| Bacterial strain | Interferon mRNA activity (unit/ml) |
|---|---|
| #319 | 360 |
| #644 | <10 |
| #746 | 15 |
| #3578 | <10 |
| pBR322DNA | <10 |

Five μg of plasmid DNA obtained from strain #319 by the Currier and Nester method was cleaved with restriction endonuclease Hind III in the same manner as mentioned above. The DNA and the recombinant plasmid βBGpBR322 DNA (the vector was pBR322) (obtained from the Institute for Molecular Biology I of University of Zurich or prepared by the method described in Nature 281, 40–46, 1979) containing rabbit β-globin gene, separately or as a mixture, were hybridized with a mixture of rabbit globin mRNA (obtained from rabbit red blood cells) (1 μg) and interferon mRNA (2.5 μg) obtained from human fibroblasts under the same conditions as mentioned above. The mRNA which formed a hybrid was injected into the oocytes of *Xenopus laevis*. The oocytes were then incubated for 15 hours in Barth's culture medium (J. Embryol. Exp. Morph. 7, 210, 1959) containing [³H] labelled histidine and [³H] labelled globin was isolated by acrylamide gel electrophoresis and determined quantitatively by fluorography according to the method described in Eur. J. Biochem. 46, 83–88, (1974). The interferon was determined by antiviral activity as described above. The synthesis of rabbit β-globin and the human interferon was determined in this way. The result is shown in Table 4 below.

TABLE 4

| DNA | Synthesized interferon activity | Amount of globin synthesized |
|---|---|---|
| #319 | 200 (units/ml) | — |
| βGpBR322 | 35 | + + + + |
| mixture of both plasmids | 160 | + + + |

From the result of this experiment it has been established that DNA of #319 has DNA (the interferon gene) which forms a hybrid specifically with the interferon mRNA.

The DNA of #319 was cleaved with several restriction endonucleases and a restriction endonuclease map, FIG. 1(a), was made by agalose electrophoresis.

Restriction endonucleases, Pst I, Bgl II and Hind III (sold by BRL, etc.) cleave #319 DNA at the sites illustrated in FIG. 1 (a).

The segments obtained by cleaving #319 DNA with restriction endonucleases Pst I and Bgl II were isolated and purified by gel electrophoresis according to the method of Tabak & Flayell (Nucleic Acids Research, vol. 5, p. 2321–2332, 1978). The segments were labelled with P according to the method of Rigby, et al. (J. Mol. Biol. vol. 113, p. 237–251, 1977) and the labelled segment was used as a probe. Several strains containing a plasmid which shows complementarity to the probe were isolated from the above ampicillin-resistant strains according to the above method of Grunstein & Hogness (Proc. Nat. Acad. Sci. U.S.A., vol. 72, p. 3961–3965, 1975), namely, colony hybridization method. Plasmid DNAs were obtained from each of the strains according to the above method of Currier-Nester and the inserted portions thereof were cleaved with a restriction endonuclease such as Hind III. The cut plasmid DNA segments were compared in length and the longest plasmid DNA segment was selected. The plasmid was named #319-13.

The restriction endonuclease map of the plasmid is illustrated in FIG. 1 (b) which substantiates that the novel plasmid has an mRNA sequence containing the mRNA sequence of #319. Primary structure (base sequence) of the mRNA sequence inserted in the plasmid of #319-13 was determined by the method of Maxam-Gilbert (Proc. Nat. Acad. Sci, U.S.A. vol. 74, p. 560–564, 1977). The primary structure is given in Table 5 below.

TABLE 5

```
        -20
    MET THR ASN LYS CYS PHE LEU LEU CYS PHE LEU LEU ALA LEU SER THR ALA LEU SER TYR
    ATG ACC AAC AAG TGT TTC CTC CTG TGC TTT CTG CTG GCT CTT TCC ACA GCT CTT TCC TAC ATG
GTC TAC TGG TTG TTC AAG AGA GAG GAC ACG AAA GAC GAC CGA GAG GAA GGT CGA GAA AGG TAC ATG
                                                                                         1
                         -10
                                                     20
                                                                        MET SER TYR

GLN ILE LEU LEU CYS PHE SER THR THR ALA LEU          GLY ARG LEU GLU
            CAA ATT CTG TTG TGC TTC TCC ACT ACA GCT CTT          GGG AGG CTT GAA
            GTT TAA GAC AAC ACG AAG AGG TGA TGT CGA GAA          CCC TCC GAA CTT
                 40                              60

ASN LEU GLY PHE ARG SER ASN PHE GLN LEU TRP GLN GLN LEU ASN GLY ARG LEU GLU
AAT TTG GGA TTC AGA AGC AAT TTT CAG CTC TGG CAA CAG TTG AAT GGG AGG CTT GAA
TTA AAC CCT AAG TCT TCG TTA AAA GTC GAG ACC GTT GTC AAC CCC TCC GAA CTT
 80                           100                              120                140

30
TYR CYS LEU LYS ASP ARG MET ASN PHE ASP PHE ILE LYS GLN LYS GLN GLN ASP SER PHE GLN LYS GLU GLU ASP ALA
TAT TGC CTC AAG GAC AGG ATG AAC TTT GAC TTT ATT AAG CAG AAG CAG CAG GAT TCT CAA AAG GAG GAC GCC
ATA ACG GAG TTC CTG TCC TAC TTG AAA CTG AAA TAA TTC GTC TTC GTC GTC CTA AGA GTT TTC CTC CTG CGG
 160                         180                           200                220
                                                                                          1

60
ALA LEU THR ILE TYR GLU MET LEU GLN ASN ILE PHE ALA ILE PHE ARG GLN ASP SER SER SER THR GLY TRP ASN GLU
GCA TTG ACC ATC TAT GAG ATG CTC CAG AAC ATC TTT GCT ATT TTC AGA CAA GAT TCA AGT ACA GGC TGG AAT GAG
CGT AAC TGG TAG ATA CTC TAC GAG GTC TTG TAG AAA CGA TAA AAG TCT GTT CTA AGT TCA TGT CCG ACC TTA CTC
240                      260                            280                300
                                                                                                   80

THR ILE VAL GLU ASN LEU LEU ALA ASN VAL TYR HIS GLN ILE ASN HIS LEU LYS THR VAL LEU GLU GLU LYS LEU GLU
ACT ATT GTT GAG AAC CTC CTG GCT AAT GTC TAT CAT CAG ATA AAC CAC CTG AAG ACA GTC CTG GAA GAA AAA CTG
TGA TAA CAA CTC TTG GAG GAC CGA TTA CAG ATA GTA GTC TAT TTG GTG GAC TTC TGT CAG GAC CTT CTT TTT GAC
 320                           340                          360                380

110
LYS GLU ASP PHE THR ARG GLY LYS LEU MET SER SER LEU HIS LEU LYS ARG TYR TYR GLY ARG ILE LEU HIS TYR LEU
AAA GAA GAT TTC ACC AGG GGA AAA CTC ATG AGC AGT CTG CAC CTG AAA AGA TAT TAT GGG AGG ATT CTG CAT TAC CTG
TTT CTT CTA AAG TGG TCC CCT TTT GAG TAC TCG TCA GAC GTG GAC TTT TCT ATA ATA CCC TCC TAA GAC GTA ATG GAC
    400                         420                        440                460

140                                                          150
LYS ALA LYS GLU TYR SER HIS CYS ALA TRP THR ILE VAL ARG VAL GLU ILE LEU ARG ASN PHE TYR PHE ILE ASN ARG LEU
AAG GCC AAG GAG TAC AGT CAC TGT GCC TGG ACC ATA GTC AGA GTG GAA ATC CTA AGG AAC TTG TAC TTT ATT AAC AGA CTG
TTC CGG TTC CTC ATG TCA GTG ACA CGG ACC TGG TAT CAG TCT CAC CTT TAG GAT TCC TTG AAC ATG AAA TAA TTG TCT GAC
 480                         500                             520                       540

160                166
LEU THR GLY TYR LEU ARG ASN
CTT ACA GGT TAC CTC CGA AAC TGA AGA TCT CCT AGC TGC CTC TGG GAC ACA ATT GCT TCA AGC ATT CTT CAA
```

TABLE 5-continued

```
GAA TGT CCA ATG GAG GCT TTG ACT TCT AGA GGA TCG GAC ACG GAG ACC CTG ACC TGT TAA CGA AGT TCG TAA GAA GTT
            560                     580                     600                     620
CCA GCA GAT GCT GTT TAA GTG ACT GAT GGC TAA ATT GAA AGG ACA CTA GAA TTT AAA CTT TAA ATT TTT ATT
GGT CGT CGA CTA CGA CAA ATT CAC TGA CTA CCG ATT ACA CGT ATA CTT TCC AGT GAT CTT CTA AAA AAA TAA
            640                     660                     680                     700
AAA TTA TGA GTT ATT ATT TAT TTT ATT TTG GAA AAT AAA TTT AAT TTA TTT AAA AAC TTT AAA AAC CTT TTT GTG CAA AAG TCA AAA AAA
TTT AAT ACT CAA TAA ATA AAT AAA TTA AAA ACC TTT TTA AAT TAA TAA AAT TTT AAA AAC CTT TTA AAC CAC GTT TTC AGT TTT TTT
            720                     740                     760
```

The DNA sequence permits prediction of the entire amino acid sequence for human fibroblast interferon (amino acids 1-166) and its putative signal peptide (amino acids −21 to −1) as shown in the line above the DNA sequences.

It is important that in the sequence there exist without any errors the base sequence (three base pairs) corresponding to the amino acid sequence from the aminoterminal to 13th amino acid of the human fibroblast interferon reported by Knight, et al. (Science vol. 207, p. 525-526, 1980). This fact establishes that the #319-13 plasmid of the present invention has the human fibroblast interferon mRNA sequence.

Further, it is apparent from the data of the primary sequence that the plasmid encompasses the entire coding region of the protein of the above mRNA and probably the coding region of the signal peptide.

Therefore, transformation of the plasmid or mRNA inserted therein to other expression plasmids enables a host such as *Escherichia coli* to produce interferon. For such purposes, the #319-13 plasmid which is named TpIF 319-13, transformed in *Escherichia coli* χ1776, has been deposited with the American Type Culture Collection, Rockville, Md. U.S.A. under accession number ATCC 31712 and is freely available to the public.

What is claimed is:

1. A DNA which consists essentially of a DNA which codes for human fibroblast $\beta_1$ interferon polypeptide.

2. A DNA consisting essentially of a DNA which codes for the amino acid sequence:

Met Thr Asn Lys Cys Leu Leu Gln Ile Ala Leu Leu Leu Cys Phe Ser
Thr Thr Ala Leu Ser Met Ser Tyr Asn Leu Leu Gly Phe Leu Gln Arg
Ser Ser Asn Phe Gln Cys Gln Lys Leu Leu Trp Gln Leu Asn Gly Arg
Leu Glu Tyr Cys Leu Lys Asp Arg Met Asn Phe Asp Ile Pro Glu Glu
Ile Lys Gln Leu Gln Gln Phe Gln Lys Glu Asp Ala Ala Leu Thr Ile
Tyr Glu Met Leu Gln Asn Ile Phe Ala Ile Phe Arg Gln Asp Ser Ser
Ser Thr Gly Trp Asn Glu Thr Ile Val Glu Asn Leu Leu Ala Asn Val
Tyr His Gln Ile Asn His Leu Lys Thr Val Leu Glu Glu Lys Leu Glu
Lys Glu Asp Phe Thr Arg Gly Lys Leu Met Ser Ser Leu His Leu Lys
Arg Tyr Tyr Gly Arg Ile Leu His Tyr Leu Lys Ala Lys Glu Tyr Ser
His Cys Ala Trp Thr Ile Val Arg Val Glu Ile Leu Arg Asn Phe Tyr
Phe Ile Asn Arg Leu Thr Gly Tyr Leu Arg Asn.

3. A DNA consisting essentially of a DNA according to claim 2 which has the base pair sequence:

```
ATG ACC AAC AAG TGT CTC CTC CAA ATT GCT CTC CTG TTG TGC TTC TCC
TAC TGG TTG TTC ACA GAG GAG GTT TAA CGA GAG GAC AAC ACG AAG AGG

ACT ACA GCT CTT TCC ATG AGC TAC AAC TTG CTT GGA TTC CTA CAA AGA
TGA TGT CGA GAA AGG TAC TCG ATG TTG AAC GAA CCT AAG CAT GTT TCT

AGC AGC AAT TTT CAG TGT CAG AAG CTC CTG TGG CAA TTG AAT GGG AGG
TCG TCG TTA AAA GTC ACA GTC TTC GAG GAC ACC GTT AAC TTA CCC TCC

CTT GAA TAT TGC CTC AAG GAC AGG ATG AAC TTT GAC ATC CCT GAG GAG
GAA CTT ATA ACG GAG TTC CTG TCC TAC TTG AAA CTG TAG GGA CTC CTC

ATT AAG CAG CTG CAG CAG TTC CAG AAG GAG GAC GCC GCA TTG ACC ATC
TAA TTC GTC GAC GTC GTC AAG GTC TTC CTC CTG CGG CGT AAC TGG TAG

TAT GAG ATG CTC CAG AAC ATC TTT GCT ATT TTC AGA CAA GAT TCA TCT
ATA CTC TAC GAG GTC TTG TAG AAA CGA TAA AAG TCT GTT CTA AGT AGA

AGC ACT GGC TGG AAT GAG ACT ATT GTT GAG AAC CTC CTG GCT AAT GTC
TCG TGA CCG ACC TTA CTC TGA TAA CAA CTC TTG GAG GAC CGA TTA CAG

TAT CAT CAG ATA AAC CAT CTG AAG ACA GTC CTG GAA GAA AAA CTG GAG
ATA GTA GTC TAT TTG GTA GAC TTC TGT CAG GAC CTT CTT TTT GAC CTC

AAA GAA GAT TTC ACC AGG GGA AAA CTC ATG AGC AGT CTG CAC CTG AAA
TTT CTT CTA AAG TGG TCC CCT TTT GAG TAC TCG TCA GAC GTG GAC TTT

AGA TAT TAT GGG AGG ATT CTG CAT TAC CTG AAG GCC AAG GAG TAC AGT
TCT ATA ATA CCC TCC TAA GAC GTA ATG GAC TTC CGG TTC CTC ATG TCA

CAC TGT GCC TGG ACC ATA GTC AGA GTG AAA ATC CTA AGG AAC TTT TAC
GTG ACA CGG ACC TGG TAT CAG TCT CAC CTT TAG GAT TCC TTG AAA ATG

TTC ATT AAC AGA CTT ACA GGT TAC CTC CGA AAC
AAG TAA TTG TCT GAA TGT CCA ATG GAG GCT TTG.
```

4. A cloned DNA consisting essentially of a DNA having the base pair sequence defined in claim 3.

5. A cloned DNA consisting essentially of a DNA which codes for the amino acid sequence defined in claim 2.

6. A DNA consisting essentially of a DNA which codes for mature human fibroblast interferon polypeptide having the amino acid sequence:

| Met | Ser | Tyr | Asn | Leu | Leu | Gly | Phe | Leu | Gln | Arg | Ser | Ser | Asn | Phe | Gln |
| Cys | Gln | Lys | Leu | Leu | Trp | Gln | Leu | Asn | Gly | Arg | Leu | Glu | Tyr | Cys | Leu |
| Lys | Asp | Arg | Met | Asn | Phe | Asp | Ile | Pro | Glu | Glu | Ile | Lys | Gln | Leu | Gln |
| Gln | Phe | Gln | Lys | Glu | Asp | Ala | Ala | Leu | Thr | Ile | Tyr | Glu | Met | Leu | Gln |
| Asn | Ile | Phe | Ala | Ile | Phe | Arg | Gln | Asp | Ser | Ser | Ser | Thr | Gly | Trp | Asn |
| Glu | Thr | Ile | Val | Glu | Asn | Leu | Leu | Ala | Asn | Val | Tyr | His | Gln | Ile | Asn |
| His | Leu | Lys | Thr | Val | Leu | Glu | Glu | Lys | Leu | Glu | Lys | Glu | Asp | Phe | Thr |
| Arg | Gly | Lys | Leu | Met | Ser | Ser | Leu | His | Leu | Lys | Arg | Tyr | Tyr | Gly | Arg |
| Ile | Leu | His | Tyr | Leu | Lys | Ala | Lys | Glu | Tyr | Ser | His | Cys | Ala | Trp | Thr |
| Ile | Val | Arg | Val | Glu | Ile | Leu | Arg | Asn | Phe | Tyr | Phe | Ile | Asn | Arg | Leu |
| Thr | Gly | Tyr | Leu | Arg | Asn. | | | | | | | | | | |

7. A DNA consisting essentially of a DNA according to claim 6 which has the base pair sequence:

```
ATG AGC TAC AAC TTG CTT GGA TTC CTA CAA AGA AGC AGC AAT TTT CAG
TAC TCG ATG TTG AAC GAA CCT AAG GAT GTT TCT TCG TCG TTA AAA GTC

TGT CAG AAG CTC CTG TGG CAA TTG AAT GGG AGG CTT GAA TAT TGC CTC
ACA GTC TTC GAG GAC ACC GTT AAC TTA CCC TCC GAA CTT ATA ACG GAG

AAG GAC AGG ATG AAC TTT GAC ATC CCT GAG GAG ATT AAG CAG CTG CAG
TTC CTG TCC TAC TTG AAA CTG TAG GGA CTC CTC TAA TTC GTC GAC GTC

CAG TTC CAG AAG GAG GAC GCC GCA TTG ACC ATC TAT GAG ATG CTC CAG
GTC AAG GTC TTC CTC CTG CGG CGT AAC TGG TAG ATA CTC TAC GAG GTC

AAC ATC TTT GCT ATT TTC AGA CAA GAT TCA TCT AGC ACT GGC TGG AAT
TTG TAG AAA CGA TAA AAG TCT GTT CTA AGT AGA TCG TGA CCG ACC TTA

GAG ACT ATT GTT GAG AAC CTC CTG GCT AAT GTC TAT CAT CAG ATA AAC
CTC TGA TAA CAA CTC TTG GAG GAC CGA TTA CAG ATA GTA GTC TAT TTG

CAT CTG AAG ACA GTC CTG GAA GAA AAA CTG GAG AAA GAA GAT TTC ACC
GTA GAC TTC TGT CAG GAC CTT CTT TTT GAC CTC TTT CTT CTA AAG TGG

AGG GGA AAA CTC ATG AGC AGT CTG CAC CTG AAA AGA TAT TAT GGG AGG
TCC CCT TTT GAG TAC TCG TCA GAC GTG GAC TTT TCT ATA ATA CCC TCC

ATT CTG CAT TAC CTG AAG GCC AAG GAG TAC AGT CAC TGT GCC TGG ACC
TAA GAC GTA ATG GAC TTC CGG TTC CTC ATG TCA GTG ACA CGG ACC TGG

ATA GTC AGA GTG GAA ATC CTA AGG AAC TTT TAC TTC ATT AAC AGA CTT
TAT CAG TCT CAC CTT TAG GAT TCC TTG AAA ATG AAG TAA TTG TCT GAA

ACA GGT TAC CTC CGA AAC
TGT CCA ATG GAG GCT TTG.
```

8. A cloned DNA consisting essentially of a DNA having the base pair sequence defined in claim 7.

9. A cloned DNA consisting essentially of a DNA which codes for a polypeptide having the amino acid sequence in claim 6.

* * * * *